US011857458B1

(12) United States Patent
Ball

(10) Patent No.: US 11,857,458 B1
(45) Date of Patent: Jan. 2, 2024

(54) FREEZABLE INSERT DEVICE

(71) Applicant: Nicholas A Ball, Linden, NC (US)

(72) Inventor: Nicholas A Ball, Linden, NC (US)

( * ) Notice: Subject to any disclaimer, the term of this patent is extended or adjusted under 35 U.S.C. 154(b) by 325 days.

(21) Appl. No.: 16/913,111

(22) Filed: Jun. 26, 2020

(51) Int. Cl.

| | |
|---|---|
| ***A61F 7/12*** | (2006.01) |
| ***A61F 7/00*** | (2006.01) |
| ***A61F 7/10*** | (2006.01) |
| ***A61F 13/34*** | (2006.01) |
| ***A61F 7/02*** | (2006.01) |
| ***A61L 31/04*** | (2006.01) |
| *A61H 23/02* | (2006.01) |

(52) U.S. Cl.
CPC .............. *A61F 7/12* (2013.01); *A61L 31/042* (2013.01); *A61F 13/34* (2013.01); *A61F 2007/005* (2013.01); *A61F 2007/0219* (2013.01); *A61F 2007/108* (2013.01); *A61H 23/02* (2013.01); *A61H 2205/087* (2013.01)

(58) Field of Classification Search
None
See application file for complete search history.

(56) References Cited

U.S. PATENT DOCUMENTS 4,239,175 A 12/1980 Straubinger
5,993,377 A * 11/1999 Hartwig .................... A61F 7/12 600/38
2006/0127542 A1 6/2006 Wachtel et al.
2007/0021809 A1* 1/2007 Cole ......................... A61F 7/12 607/113
2012/0282317 A1 11/2012 Ekstein
2013/0011531 A1* 1/2013 Wolf ........................ A23G 9/26 249/97
2013/0023970 A1* 1/2013 Cull .......................... A61F 7/12 607/113
2014/0316485 A1* 10/2014 Ackermann ....... A61N 1/36132 607/53
2017/0239447 A1* 8/2017 Yang ................. A61M 25/0053
2020/0323683 A1* 10/2020 Yoskowitz ................ A61F 7/12

OTHER PUBLICATIONS

"Ice Ice Baby Vagina 'ice pops' made from condoms with frozen water inside ease new mums' pain after childbirth", by Andrea Downey. Newspaper Article [online]. © News Group Newspapers Limited [published Apr. 11, 2017; retrieved on Dec. 14, 2017]. Retrieved from the Internet: <URL: https://www.thesun.co.uk/living/3306053/new-dad-fills-condoms-with-water-and-freezes-them-to-ease-wifes-vagina-pain-after-childbirth/>.
4 Pops Maker. Product Listing [online]. © 2001-2016 The Prairie Moon Company [retrieved on Dec. 14, 2017]. Retrieved from the Internet: <URL: http://www.prairiemoon.biz/4popsmaker.html>.

* cited by examiner

*Primary Examiner* — Joanne M Rodden
*Assistant Examiner* — Nora W Rhodes
(74) *Attorney, Agent, or Firm* — Cramer Patent & Design PLLC; Aaron R. Cramer

(57) ABSTRACT

A freezable insert includes a mold having at least six (6) cylindrical forms and a corresponding number of flexible plastic handles which upon insertion into each form containing a non-toxic freezable substance creates at least six (6) frozen cylindrical forms each particularly suitable for removably insertion into a vagina.

10 Claims, 5 Drawing Sheets

10
25
30
15
20

FREEZABLE INSERT DEVICE

RELATED APPLICATIONS

None.

FIELD OF THE INVENTION

The present invention relates to a freezable insert device and more specifically to a freezable insert device for a vagina.

BACKGROUND OF THE INVENTION

As women enter menopause, their body undergoes physiological changes, many of which are not pleasant. One of the most common symptoms are hot flashes in which a quick feeling of heat, accompanied by sweating and perhaps a red flushed face is present. These hot flashes may also happen at night making it difficult to sleep.

A standard method of treatment is to encourage the sufferer to stay cool, perhaps with light clothes or even an ice pack which can be quickly pressed into service. However, these treatment methods are often not enough to help those who suffer from the most severe of hot flashes. Accordingly, there exists a need for a means by which women who suffer from hot flashes or other temperature related maladies can receive quick and effective relief and comfort. The development of the frozen insert device fulfills this need.

SUMMARY OF THE INVENTION

The principles of the present invention provide for a freezable insert device which comprises a freezable core assembly which is placed in a women's vagina to aid in reducing one or more menopausal symptoms. The freezable core assembly includes a first end, a second end and a string attached to a loop to facilitate removal of the freezable insert device from the woman's vagina. The string is extended from a second end of the freezable core assembly. The freezable core assembly may be generally tapered at the first end. The first end of the core assembly may be provided with a rounded tip which is inserted first into the woman's vagina.

The proximal end of the core assembly may be provided with a flexible handle to aid in insertion and removal of the freezable insert device. The flexible handle may be made of material selected from the group consisting of medical grade plastic, silicone, or latex. The core assembly may be filled with non-toxic gel. The non-toxic gel may be an ingredient selected from the group consisting of hydroxyethyl cellulose, polyacrylate, or vinyl-coated silica gel.

The non-toxic gel retains its temperature in a safe manner and releases energy in a controlled and steady state manner. The loop may be made of material selected from the group consisting of medical grade plastic, silicone, or latex. A vibrating applicator may allow for easier insertion or application of the freezable insert device. The vibrating applicator may be a simple offset weight on a motor that is powered by in internal rechargeable battery in a simple series circuit with a power switch. A charging port may be provided to recharge the internal battery. A holding stand may hold up to 6 of the freezable insert devices in individual upright compartments.

The freezable insert also may comprise a sidewall to provide structural rigidity to the freezable insert device. The sidewall provides a sufficient thermal gradient to limit excessive temperatures from being transferred out of the core assembly. The freezable insert device may provide a cooling capability by placing it in a standard refrigerator prior to use.

The freezable insert device may be warmed by placing it in a pot of warm water prior to usage. The sidewall may be made of material selected from the group consisting of medical grade plastic, silicone, or latex. The freezable insert device may be in the range of five to thirteen centimeters in length and in the range of one point five to three point five centimeters in diameter.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY

Figure 1:
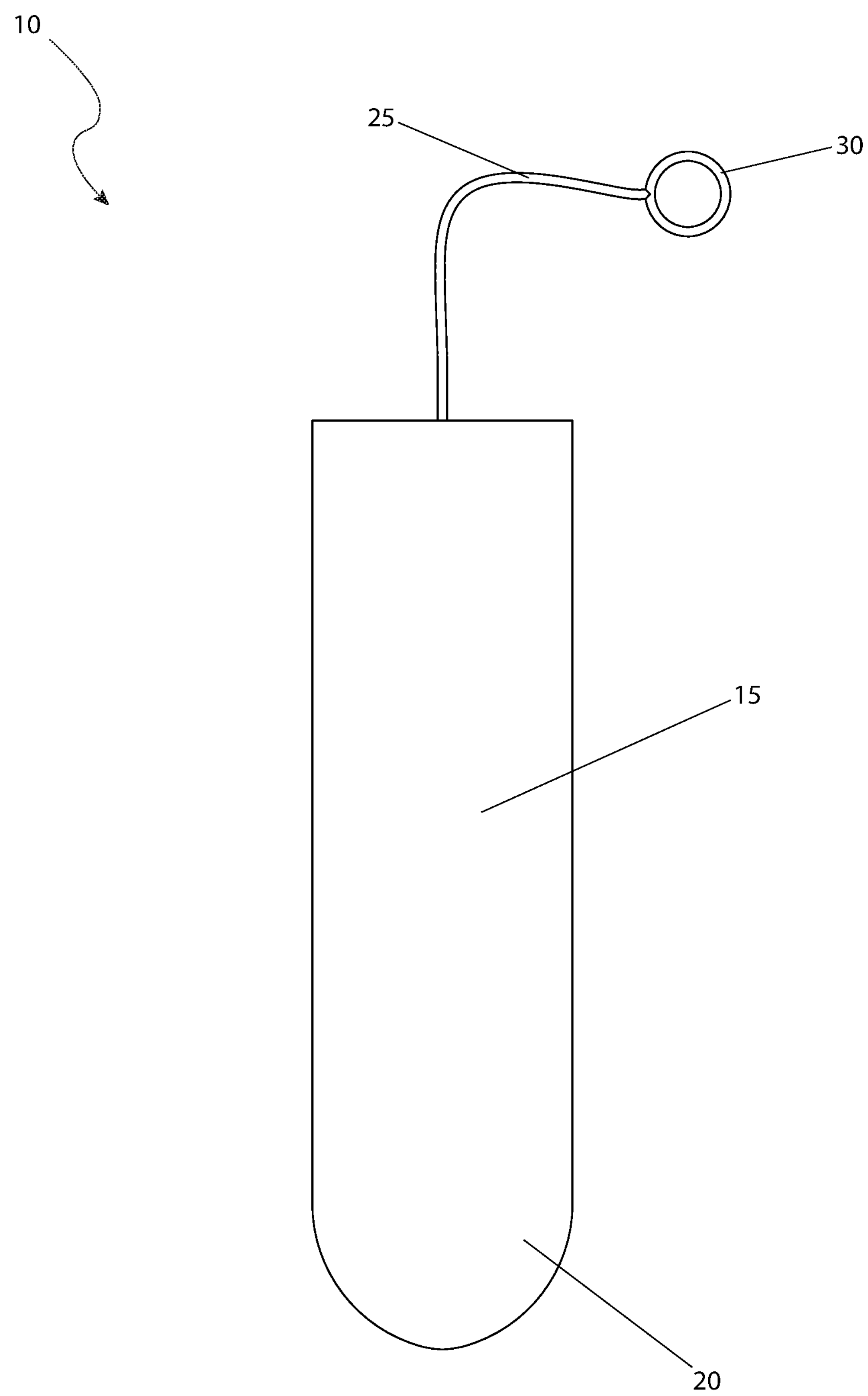
FIG. 1 is a front view of the freezable insert device, according to the preferred embodiment of the present invention.

10 freezable insert device
15 core assembly
20 rounded tip
25 flexible handle
30 loop
35 sidewall
40 non-toxic gel
45 vibrating applicator
50 power switch
55 charging port
60 holding stand
65 upright compartment
70 opening

DESCRIPTION OF THE PREFERRED EMBODIMENTS

The best mode for carrying out the invention is presented in terms of its preferred embodiment, herein depicted within FIGS. 1 through 5. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms “a” and “an” herein do not denote a limitation of quantity, but rather denote the presence of at least one (1) of the referenced items.

1. Detailed Description of the Figures

Referring now to FIG. 1, a front view of the freezable insert device 10, according to the preferred embodiment of the present invention is disclosed. The freezable insert device 10 (herein also described as the “device”) 10, provides a freezable insert particularly suited to be placed in a women’s vagina to aid in the reduction of menopausal symptoms of hot flashes and other physical abnormalities. The device 10 provides for a freezable core assembly 15 that is generally tapered in design. The distal end of the core assembly 15 is provided with a rounded tip 20 which is inserted first into the vagina. The opposite or proximal end of the core assembly 15 is provided with a flexible handle 25 to aid in insertion and removal of the device 10. A loop 30 is disposed on the distal end of the flexible handle 25 to facilitate gripping. It is also envisioned that a string 25 may be attached to the loop 30 to facilitate removal of the device 10 from the vagina. It is envisioned that the device 10 would be made available in multiple sizes to fit all sizes of users. The range of size measurements would vary between five to thirteen centimeters (5-13 cm) in length, and diameters that vary from one-and-a-half to three and a half centimeters (1.5-3.5 cm).

Figure 2:
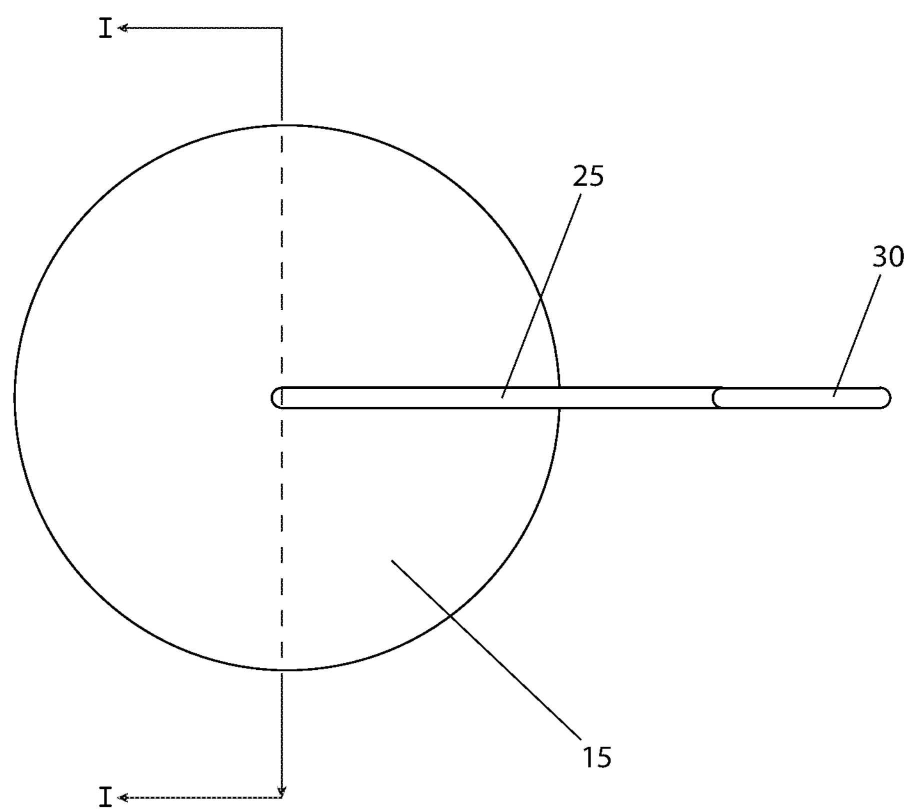
FIG. 2 is a top view of the freezable insert device, according to the preferred embodiment of the present invention.

Referring next to FIG. 2, a top view of the device 10, according to the preferred embodiment of the present invention is depicted. The top view of the device 10 discloses its circular nature. As expected, the flexible handle 25 and loop 30 remain visible.

Figure 3:
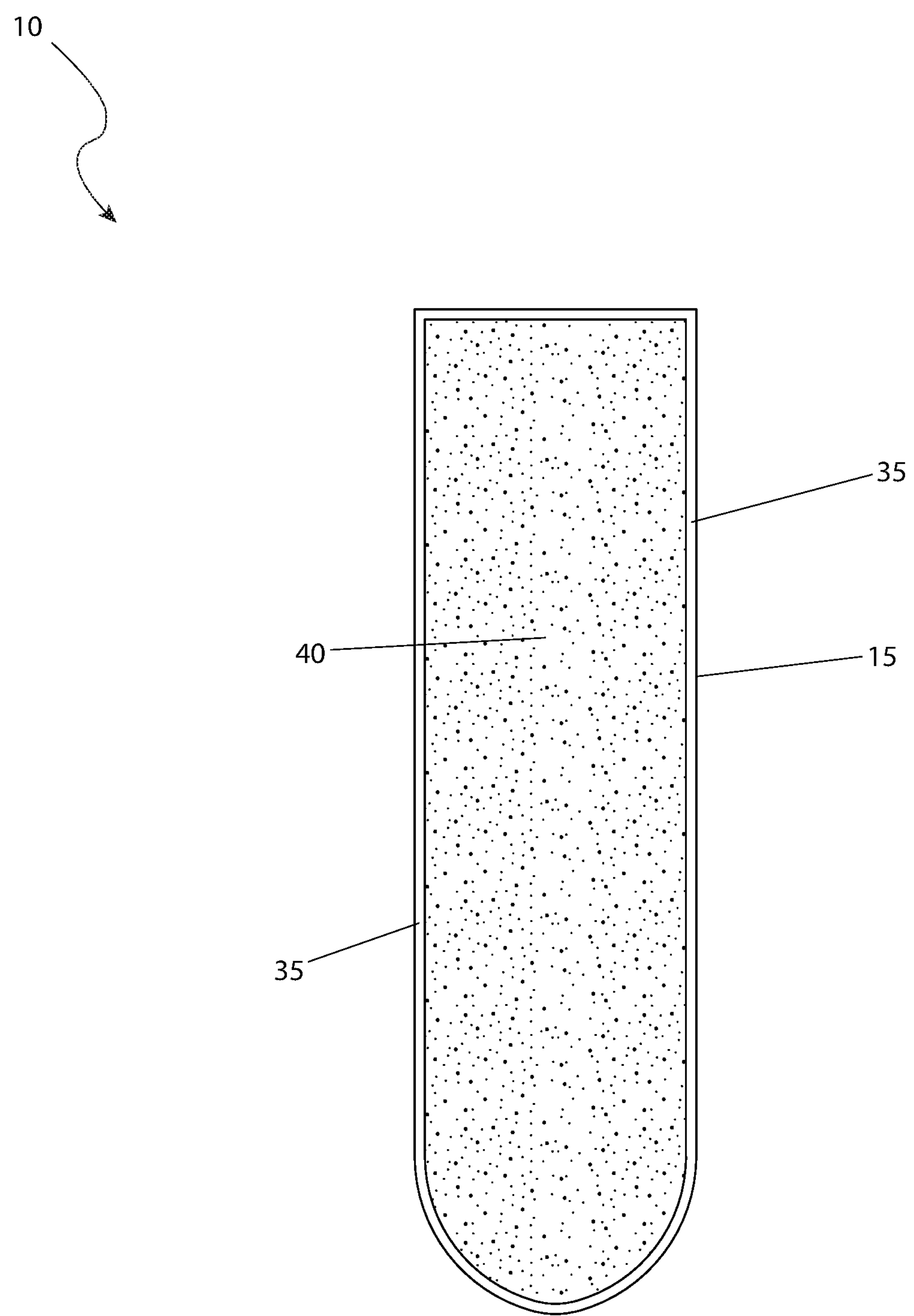
FIG. 3 is a sectional view of the freezable insert device, as seen along a line I-I, as shown in FIG. 2, according to the preferred embodiment of the present invention.

Referring now to FIG. 3, a sectional view of the device 10, as seen along a line I-I, as shown in FIG. 2, according to the preferred embodiment of the present invention is shown. This view provides clarification on the interior construction of the core assembly 15. A sidewall 35 of sufficient thickness to provide structural rigidity to the invention. The sidewall 35 also provides a sufficient thermal gradient to excessive temperatures (either too hot or too cold) from being transferred out of the core assembly 15. It is envisioned that the sidewall 35 as well as other components of the device 10 such as the flexible handle 25 and the loop 30 would be made of medical grade plastic, silicone, latex, or similar material. The exact material of construction is not intended to be a limiting factor of the present invention. The interior of the core assembly 15 is filled with non-toxic gel 40 material including ingredients such as hydroxyethyl cellulose, polyacrylate, and/or vinyl-coated silica gel. The exact product materials as used in the non-toxic gel 40 are not intended to be a limiting factor of the present invention. While the present invention is intended to provide cooling capabilities by placing it in a standard refrigerator prior to use, it is also envisioned that the device 10—could be warmed by placing it in a pot of warm water prior to usage as well. The non-toxic gel 40 will retain the applied temperature in a safe manner and release it in a controlled and steady state manner. The sidewall 35 is in direct contact with the freezable core assembly 15 and is disposed around the perimeter of the freezable core assembly 15.

Figure 4:
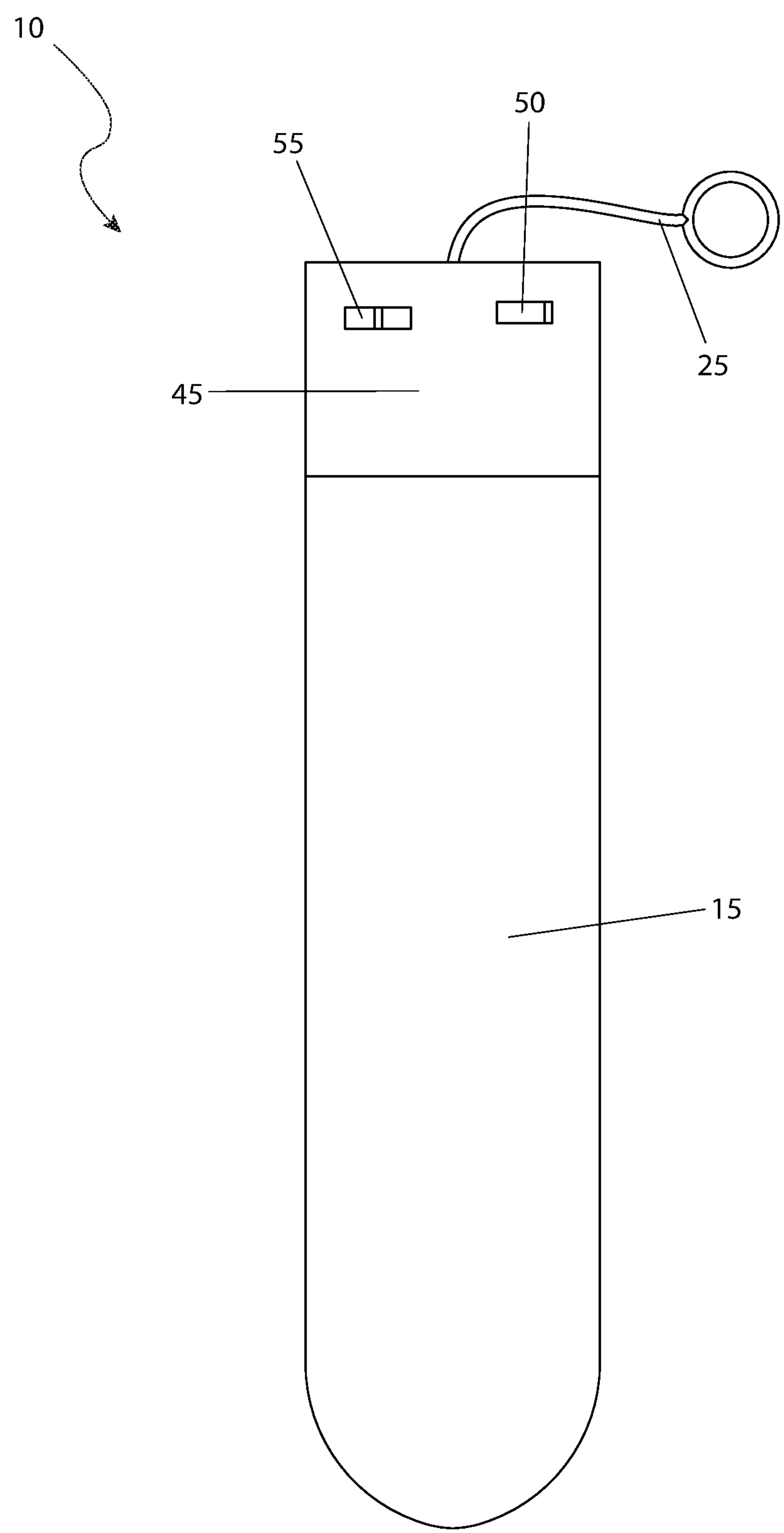
FIG. 4 is a front view of the freezable insert device, shown with a vibrating applicator, according to the preferred embodiment of the present invention; and, FIG. 5 is a perspective view of the freezable insert device, as used with the freezable vaginal insert device, according to the preferred embodiment of the present invention.

Referring next to FIG. 4, a front view of the device 10, shown with a vibrating applicator 45, according to the preferred embodiment of the present invention is disclosed. The vibrating applicator 45 attaches to the flexible handle 25 via friction fit. It is intended that the vibrating applicator 45 allows for easier insertion or application of the device 10. The vibrating applicator 45 is envisioned to be a simple offset weight on a motor that is powered by in internal rechargeable battery in a simple series circuit with a power switch 50. A charging port 55 is also provided to allow for recharging of the internal battery. It is envisioned that the vibrating applicator 45 may be used during the insertion or application process of the core assembly 15 only or may be left in place during the entire usage cycle of the device 10. The removable nature of the vibrating applicator 45 allows it to be moved to different device 10 should more than one (1) cooling (or heating) treatment afforded by a single device 10 be required.

Figure 5:
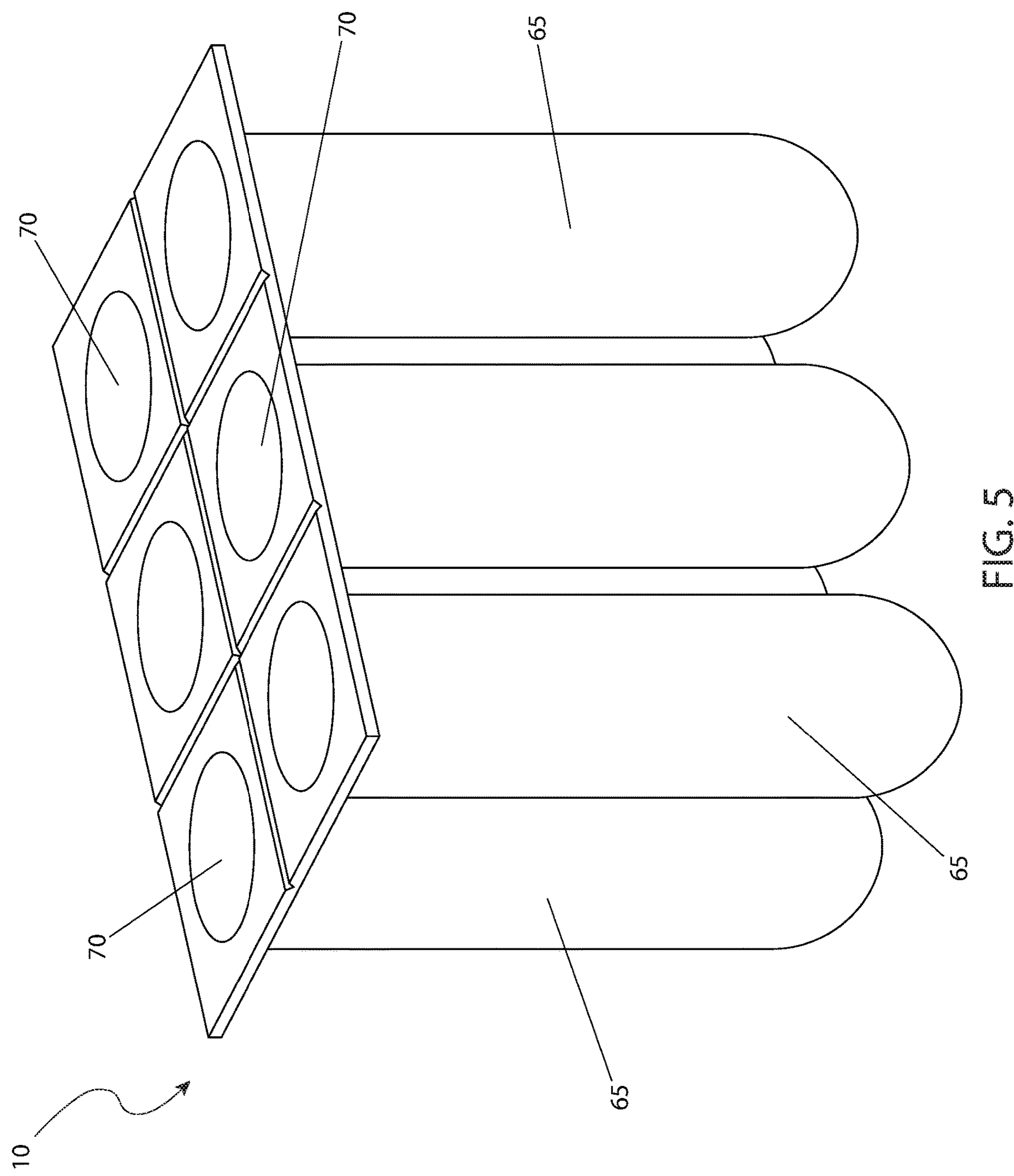

Referring finally to FIG. 5, a perspective view of the holding stand 60, as used with the device 10, according to the preferred embodiment of the present invention is depicted. The holding stand 60 holds up to six (6) devices 10 in individual upright compartments 65, via upper openings 70. The device 10 would simple be inserted in an upright manner while in a freezer compartment. The storage capabilities provided by the holding stand 60 aid in maintaining clean and sanitary conditions inside of a freezer as well as an organizational aid to allow for ease of access. It is envisioned that the holding stand 60 would be made of a plastic in a one-piece molding process.

2. Operation of the Preferred Embodiment

The preferred embodiment of the present invention can be utilized by the common user in a simple and effortless manner with little or no training. It is envisioned that the device 10 would be constructed in general accordance with FIG. 1 through FIG. 5. The user would procure the device 10 from conventional procurement channels such as medical supply houses, discount stores, drug stores, mail order and internet supply houses and the like. Special attention would be paid to the overall size of the core assembly 15 with respect to the user so maximum comfort and cooling capabilities can be provided.

After procurement and prior to utilization, the device 10 would be prepared in the following manner: the device 10 would be cleaned prior to initial use and in between each usage cycle; multiple device 10 would be placed in the upright compartments 65 of the holding stand 60 and stored in a conventional freezer until frozen; should warming capabilities be required, the device 10 would be placed in a pot of warm water for several minutes. At this point in time, the device 10 is ready for usage.

During utilization of the device 10, the following procedure would be initiated: the user would hold the device 10 by the flexible handle 25 and insert it into the vagina; cooling or warming action as afforded by prior placement in a freezer or warm water respectively is then imparted; said cooling action would reduce symptoms of hot flashes and other physical abnormalities during menopause or other obstetric and gynecological treatments where temperature and/or swelling in the vaginal area needs to be modified; should the temperature of the device 10 be modified such that it is no longer effective; the user may remove the first device 10 and replace with another. The user may also place the vibrating applicator 45 on the device 10 to aid in insertion. As aforementioned described, the vibrating applicator 45 may be used during the insertion or application process of the device 10 only or may be left in place during the entire usage cycle of the device 10.

After use of the device 10, it is carefully cleaned, sanitized, and stored in the holding stand 60 until needed again at future time in a repeating and cyclical manner.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. A freezable insert device, consisting of:

a freezable core assembly placed in a women's vagina to aid in reducing one or more menopausal symptoms, the freezable core assembly includes a first end and a second end;

a string attached to a loop to facilitate removal of the freezable insert device from the woman's vagina, the string is extended from a second end of the freezable core assembly and the loop is disposed on a distal end of the string; and a sidewall to provide structural rigidity to the freezable insert device, the sidewall providing a sufficient thermal gradient to limit excessive temperatures from being transferred out of the freezable core assembly;

wherein the sidewall is in direct contact with the freezable core assembly and is disposed around the perimeter of the freezable core assembly;

wherein the interior of the freezable core assembly is filled with non-toxic gel; and wherein the non-toxic gel is an ingredient selected from the group consisting of hydroxyethyl cellulose, polyacrylate, or vinyl-coated silica gel;

wherein the freezable core assembly is generally tapered at the first end.

2. The freezable insert device according to claim 1, wherein the first end of the freezable core assembly is provided with a rounded tip which is inserted first into the woman's vagina.

3. The freezable insert device according to claim 1, wherein the proximal end of the freezable core assembly includes the string to aid in insertion and removal of the freezable insert device.

4. The freezable insert device according to claim 3, wherein the string is made of material selected from the group consisting of medical grade plastic, silicone, or latex.

5. The freezable insert device according to claim 1, wherein the non-toxic gel retains its temperature in a safe manner and releases energy in a controlled and steady state manner.

6. The freezable insert device according to claim 1, wherein the loop is made of material selected from the group consisting of medical grade plastic, silicone, or latex.

7. The freezable insert device according to claim 1, wherein the freezable insert device provides a cooling capability by placing it in a standard refrigerator prior to use.

8. The freezable insert device according to claim 1, wherein the freezable insert device is warmed by placing it in a pot of warm water prior to usage.

9. The freezable insert device according to claim 1, wherein the sidewall is made of material selected from the group consisting of medical grade plastic, silicone, or latex.

10. The freezable insert device according to claim 1, wherein the freezable insert device is in the range of 5 to 13 cm. in length and in the range of 1.5 to 3.5 cm. in diameter.

* * * * *